United States Patent [19]

Godfrey et al.

[11] 4,062,229

[45] Dec. 13, 1977

[54] METHOD OF TESTING THE INTEGRITY OF INSTALLED ROCK BOLTS

[75] Inventors: David E. Godfrey; Norman R. Kuchar, both of Burnt Hills, N.Y.

[73] Assignee: General Electric Company, Schenectady, N.Y.

[21] Appl. No.: 770,697

[22] Filed: Feb. 22, 1977

[51] Int. Cl.[2] .......................................... G01N 29/00
[52] U.S. Cl. ...................................... 73/88 F; 73/582
[58] Field of Search ...................... 73/88 F, 67.2, 67.1, 73/88 B; 116/DIG. 34

[56] References Cited

U.S. PATENT DOCUMENTS 3,307,393 3/1967 Kessler .......................... 73/88 F UX
3,960,009 6/1976 Roepke et al. ........................ 73/88 F
3,975,948 8/1976 Makino et al. .................... 73/88 F X Primary Examiner—Jerry W. Myracle
Attorney, Agent, or Firm—Donald R. Campbell; Joseph T. Cohen; Jerome C. Squillaro

[57] ABSTRACT

The bond integrity of resin grouted rock bolts or roof bolts anchored within the ceiling in underground mines is tested by inducing broadband vibrations and measuring the resonant frequencies of the axial and transverse vibration modes. Voids in the resin grout or imperfect bonding cause shifts in the resonant frequencies. The tension in expansion nut rock bolts is determined from the resonant frequency of the transverse vibration mode.

8 Claims, 8 Drawing Figures

U.S. Patent  Dec. 13, 1977  Sheet 1 of 2  4,062,229
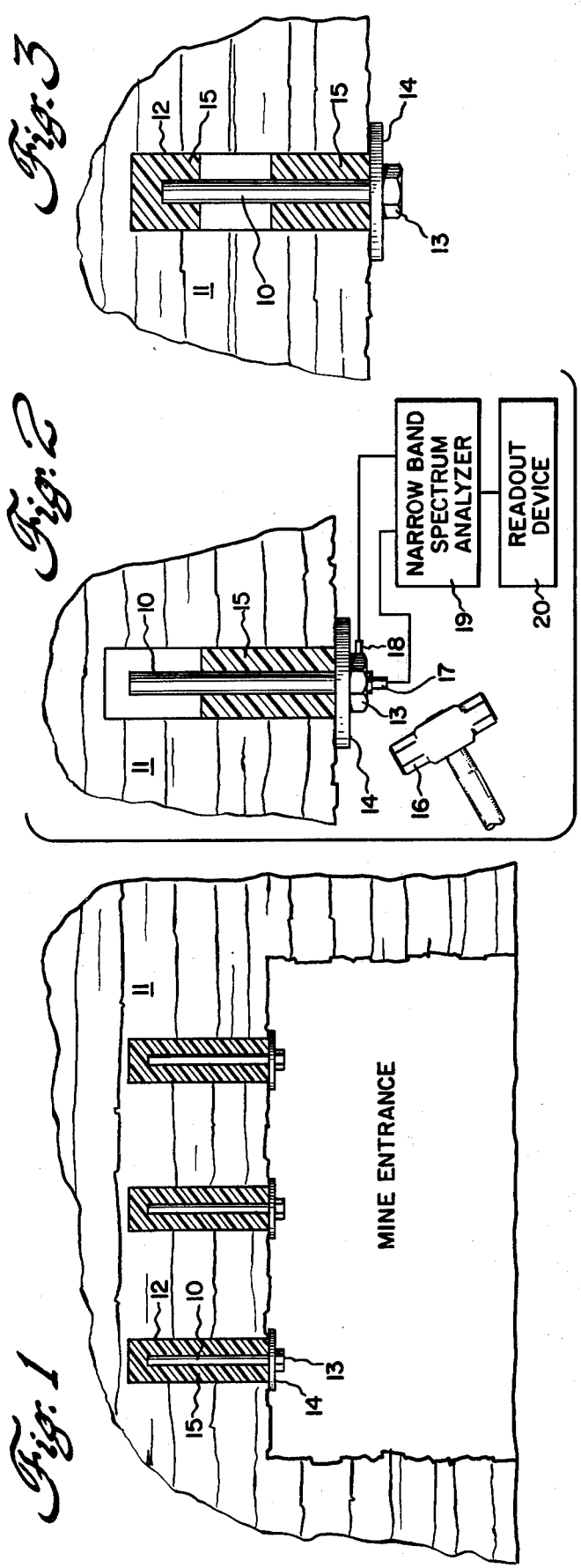
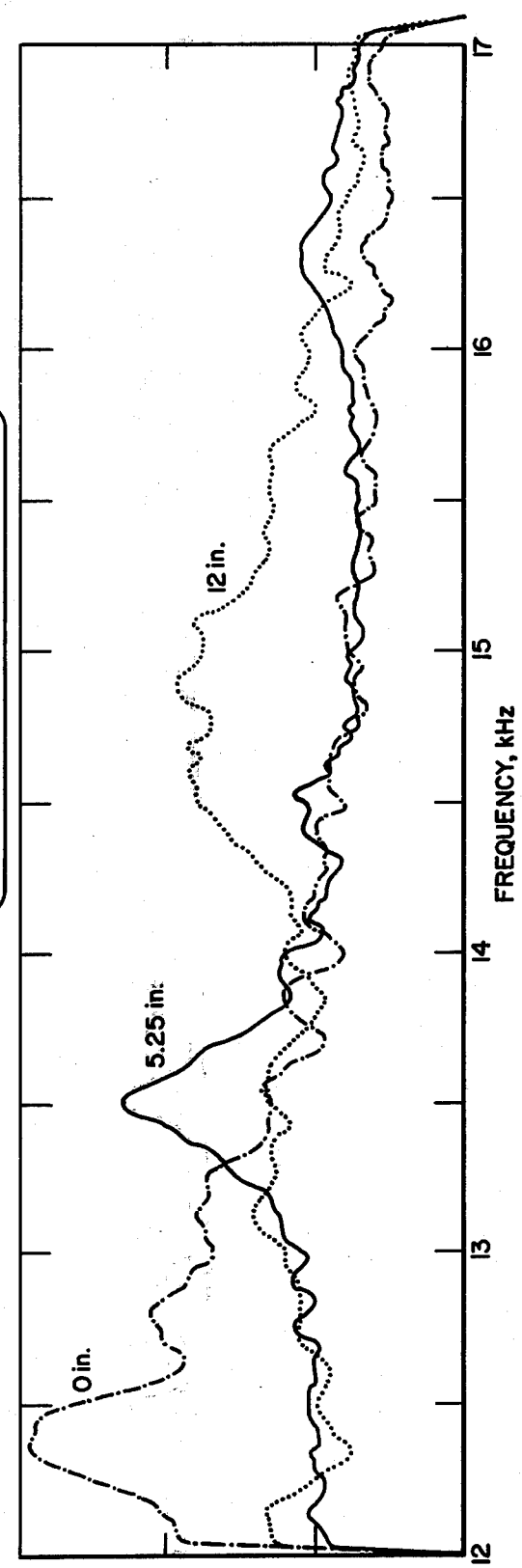

METHOD OF TESTING THE INTEGRITY OF INSTALLED ROCK BOLTS

BACKGROUND OF THE INVENTION

This invention relates to a method of testing the integrity of rock bolts anchored within rock strata or similar materials, and more particularly to testing the integrity of grouted rock bolts by determining the resonant frequencies of selected vibration modes. The method is also applicable to testing the tension of expansion nut rock bolts.

Steel roof bolts or rock bolts are used extensively in underground mining to support the ceilings of shafts and tunnels. The bolts, 2 to 8 feet in length, are anchored in the ceiling by resin grouting or by expansion nuts, thus trying the strata of rock together to create a beam which supports the overburden, using the side walls or pillars as foundations. Roof bolts with a typical diameter of 1 inch are inserted into predrilled holes with a bolt head brazed to one end of the bolt supporting a rectangular plate functioning as a washer. The bolts are held in place by an expansion nut at the top of the bolt or by the newer technique in which the bolt is fully grouted to the inside of the hole with polyester resin. In both cases, the roof bolt binds the rock layers together to form the strata into a beam. In the expansion nut method, tensioning of the bolt applies a compressive stress to the strata, and the friction between the layers as a result of this stress provides the shear stress needed to restrict horizontal movements of the layers, prevent buckling, and give the roof span a load carrying capability. With the fully grouted resin bolt, the resin binds the rock strata together and prevents horizontal movement without tensioning the bolt.

No method is presently defined for checking the joint integrity between the resin grouted bolt and the roof and, therefore, how well the roof bolt is anchored in the ceiling. The older expansion nut system has been checked by applying torque to the bolt which gives a measure of the tension in the bolt. This has no meaning for the grouted bolt because voids in the resin can exist which reduce the effectiveness of the bolt, but a torque could still be applied to the bolt head. Other tension measuring schemes such as the ultrasonic forced vibration technique and a liquid crystal, strain measurement technique are similarly applicable only to expansion nut roof bolts.

A method is needed to test grouted roof bolts or rock bolts to see that they are properly grouted and detect poor roof bolting which could cause roof falls. The present method is applicable to expanison type rock bolts as well.

SUMMARY OF THE INVENTION

The integrity of the anchoring of a rock bolt installed within an elogated hole in rock strata or similar substances is tested by measuring the vibration response of the bolt to broadband axial and/or transverse vibrations induced by striking the bolt base. The resonant frequencies of a partially grouted bolt are different from those of a fully grouted bolt and can be interpreted to give the degree of bonding between the resin and bolt and also the axial extent of a void in the grout material. In the case of the expansion nut rock bolt, tension variations in the bolt are detected as shifts in the measured resonant frequency. Applications include checking rock bolts in underground mine shafts and in tunnels.

To test the integrity of a resin grouted rock bolt according to the preferred method, the externally accessible base of the rock bolt is tapped with a hammer or other hard object to induce acoustic vibrations therein and sequentally excite the axial and transverse vibration modes. The bolt vibrations are sensed and electrical signals representative of the vibrations are generated. The amplitudes of the electrical signals are measured at a plurality of discrete narrow frequency bands and the resonant frequency of each vibration mode is derived. For the axial vibration mode the resonant frequency is indicative of the effective bonded bolt length, while for the transverse vibration mode the resonant frequency is indicative of the axial length of a void. Using known data of resonant frequency versus this desired information, the bonded bolt length and void length are ascertained. To determine tension in an expansion nut rock bolt, the bolt base is tapped to excite the transverse vibration mode and the resonant frequency is derived in the same manner. The acutal tension can be ascertained from data of resonant frequency versus tension; a poorly anchored bolt with low tension exhibits a reduced resonant frequency.

BRIEF DESCRIPTION OF THE DRAWINGS

FIG. 1 is a schematic elevational view, partially in section, of a mine entrance with several rock bolts anchored in the ceiling rock strata by resin grouting;

FIG. 2 is an elevational view partly in cross section of an installed grouted rock bolt with a void in the resin grout at the top of the predrilled hole, and further illustrating bolt integrity test equipment;

FIG. 3 is similar to FIG. 2 and shows a defective grouted rock bolt with a void in the resin grout at a different location than in FIG. 2;

FIG. 4 is a plot of a portion of the amplitude versus frequency spectrum in the axial vibration mode for several depths of resin grout;

DESCRIPTION OF THE PREFERRED EMBODIMENTS

Figure 5:
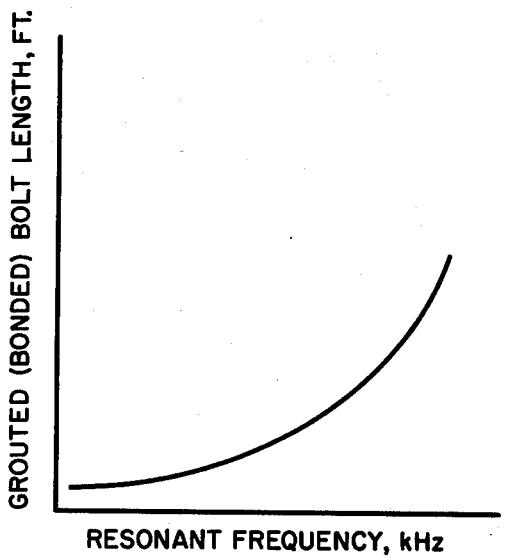
FIG. 5 is a curve of grouted or bonded bolt length versus resonant frequency for the axial vibration mode.

Although the invention has general application to checking how well a rock bolt is anchored within rock strata or similar rock-like substances such as cement or a brick wall, the preferred embodiment is explained with regard to checking the bond integrity of a grouted rock bolt in the roof of an underground mine or tunnel. The grout material commonly used for this purpose is polyester resin. Voids in the resin grout and regions of poor bonding are detected by inducting acoustic vibrations in the bolt to excite the axial and transverse vibration modes, sensing the bolt vibrations, and obtaining the resonant frequencies of the two vibration modes. The axial extent of a void and the degree of bonding between the rock bolt and roof are determined by conversion of resonant frequency for the axial vibration mode to grouted or bonded bolt length, and by conversion of a resonant frequency for the transverse vibration mode to void axial length, both by using known data for the bolt size and diameter. Checks can be made on the bolt immediately after installation as well as after a period of time during which degradation might occur. This helps to insure miner and worker safety from roof fall accidents.

In FIG. 1, the roof of a mine entrance tunnel is reinforced by a plurality of resin grouted rock bolts 10 anchored several feet within the strata of rock 11 overlying the tunnel. Rock bolts 10 typically are made of 1 inch diameter steel with a length of 2 to 8 feet. The bolts are inserted into elongated, predrilled holes 12 in the ceiling rock strata with a nut 13 functioning as a bolt head brazed to the lower end of the bolt in engagement with a rectangular plate 14 used as a washer. The bolts are held in or anchored by being fully grouted to the inside of the hole with resin grout 15. As was previously mentioned, the several grouted rock bolts in combination bind the rock layers together to form the strata into a beam. During installation of the grout material, bags of resin and catalyst are inserted into elongated hole 12 and then pierced, and the bolt is turned so that corrugations on the external surface of the bolt mix together the resin and catalyst. There may be gaps in the hardended resin grout after installation for various reasons, such as failure of the grout material to fill up the entire hole or leakage laterally into cracks between the rock layers. There may also be degradation of of the resin grout over a period of time or shifting of the strata of rock. For any of these reasons, there may be voids or gaps in the resin grout which if undetected could lead to a weakened roof structure condition.

FIG. 2 illustrates a common type of defective bond between the rock bolt and inside of the hole wherein the void in the resin grout is at the top of the hole exposing the upper end of bolt 10. In FIG. 3 the void occurs between the ends of the resin grout, exposing an intermediate portion of bolt 10. The basic concept of the present method for checking the bond integrity is to measure the vibration response of the rock bolt to longitudinal and transverse waves induced by tapping the externally accessible bolt base. A bolt only partially grouted in resin will vibrate differently than one fully grouted. Longitudinal waves propagating along the bolt give rise to a vibrating structure whose resonant frequency depends on the length of bonded resin. For transverse waves, the bolt portion in a void vibrates freely, and the measured resonant frequency of the free vibrating bolt length decreases as the axial length of void increases. The two resonant frequencies are then correlated with known data, standard for all bolts with the same length and diameter, of resonant frequency versus grouted bolt length and versus void length. In practicing the method, the externally accessible bolt base or bolt head is tapped with a metal object such as hammer 16 in the axial direction and then in the transverse direction. Striking the base of the bolt induces broadband sound vibrations in the bolt and excites, respectively, the axial vibration mode and the transverse vibration mode. Acoustic vibrations up to about 20 kHz are of interest for this application. Axial and transverse accelerometers 17 and 18 or other suitable acoustic transducers are mounted on the bolt base to sense the vibrations of the rock bolt and separately generate electrical signals representative of the axial and transverse vibrations. The electrical signals are fed to a narrow band spectrum analyzer 19 to measure the amplitude of the electrical signals at a plurality of discrete narrow frequency bands covering a predetermined frequency range. The peak amplitudes, of course, indicate the resonant frequencies of the axial and transverse vibration modes. A readout device 20 associated with the narrow band spectrum analyzer can be, for example, a cathode ray tube, but for use by mine personnel is provided in a simpler form, indicating directly the measured resonant frequencies or effective bonded bolt length and void length.

A disscussion of the theoretical aspects of the invention will facilitate understanding the method. First, consider the axial vibration mode. The natural frequencies are:

$$f_i = (a_i/L) \sqrt{(gE/\rho)} \qquad (1)$$

where
 $\rho$ = density
 $E$ = effective modulus of elasticity
 $L$ = effective length of vibrating structure
 $g$ = acceleration of gravity, and
 $a_i$ = known constants which depend on boundary conditions of the structure.

When resin is added, the effective modulus or stiffness of the rod increases and the frequencies of the rod increase. The length parameter also gives rise to a detectable frequency pattern. With no resin, the effective length is the length of the rod and the axial wave generated by striking the base of the bolt reflects off the free end. With the addition of resin, a frequency shift appears, associated with rod length bonded by the resin. Hence the frequency indicates the bonded length of the bolt. For example, a system consisting of a bolt with a void in the resin (FIG. 2) or an imperfectly bonded bolt, such as one wih multiple samll voids, will have a lower vibration frequency than a completely bonded bolt.

The transverse mode of vibration is characterized by the following frequency equation:

$$f_i = (b_i/L^2) \sqrt{gEI/W} \qquad (2)$$

where
 $b_i$ = known constants which depend on boundary conditions of the structure.
 $L$ = length of free vibrating structure,
 $g$ = acceleration of gravity,
 $E$ = modulus of elasticity,
 $I$ = moment of inertia of the cross-sectional area of the structure about the netural surface, and
 $W$ = weight per unit length of free vibrating structure.

As resin is added, L changes as the length of free rod decreases. When voids are present at the bolt end, as in FIG. 2, L will be equal to the length of free bolt, considering the bolt to be clamped at the resin surface. When intermediate voids are present, as in FIG. 3, L will be equal to the void length, considering the rod to be clamped at each resin surface. Frequencies associated with lengths other than free portions of the rod will be strongly damped causing these signals to be much lower in amplitude. On the other hand, frequencies associated with the free portions of a rod are pronounced and easily detected with accelerometers mounted to measure the transverse vibrations.

Experimental data of amplitude versus frequency in kilohertz is plotted in FIG. 4 for the axial vibration mode. The data is for a hole 1.25 inches in diameter and 12 inches long, and a 1 inch diameter steel rod. The rod was tapped with a hammer in the axial direction to induce vibrations, which were measured with an accelerometer and recorded on magnetic tape. As resin was added by increments to simulate various lengths of grouting, the data was analyzed for its spectral or frequency content using a spectral analyzer. A portion of the spectra for axial vibration with resin depths of 0, 5.25, and 12 inches is illustrated, and it can be seen that the peaks shift monotonically from 12.4 kHz to 14.9 kHz as the resin depth increased from 0 to 12 inches, i.e., the free length of the bolt decreased.

Figure 6:
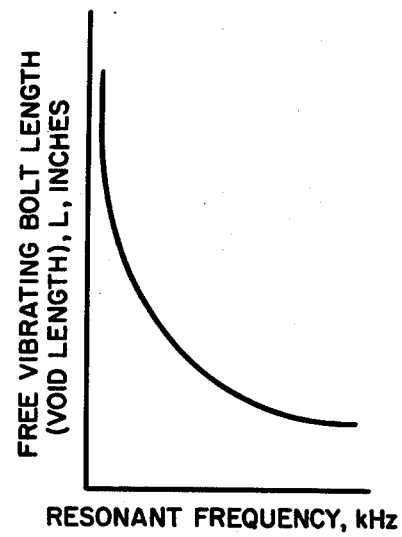
FIG. 6 is a curve of free vibrating bolt length (void length) versus resonant frequency for the transverse vibration mode.

Having measured the resonant frequency for the axial vibration mode, the grouted bolt length can be determined by reference to the curve in FIG. 5. The curve applies to a given bolt length and diameter and is plotted from experimental data. The resonant frequency for the transverse vibration mode is then ascertained by striking the bolt base in the transverse direction, sensing the transverse vibrations, and measuring the amplitude of the electrical signal at discrete narrow frequency bands to derive the resonant frequency. By reference to the curve in FIG. 6 of free vibrating bolt length versus resonant frequency, which is also a standard curve for the bolt size and diameter plotted from experimental data, the axial length of the void along the bolt is determined.

Test equipment for resin bolt integrity may have a readout indication in various forms. The measured resonant frequencies can be displayed digitally, or can be shown approximately by a series of lamp indicators covering adjacent frequency ranges each with upper and lower limits. The void length or bonded bolt length is then read off by the operator from the standard curves. Alternatively, the test equipment can include logic for converting the measured resonant frequencies to void length and bonded bolt length which are displayed directly to the operator. A switch is provided to manually set the bolt length and diameter. Another form of readout is a simple go-no go indication of a defective resin bond as, for example, by a lamp which lights whenever the grouted bolt length is low or void length exceeds a predetermined minimum. The testing device may also include a spring-loaded metal mass for striking the bolt base to induce acoustic vibrations.

Figure 7:
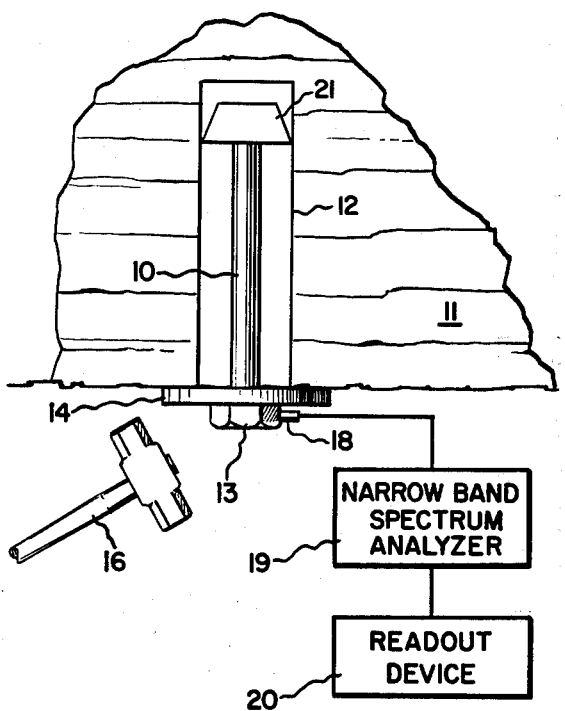
FIG. 7 is an elevational view partly in cross section of an installed expansion nut rock bolt with bolt integrity test equipment similar to that in FIG. 2.

The method is also applicable to testing the anchoring integrity of rock bolts attached with expansion nuts. For this case, tension variations in the bolt cause the vibration frequency changes. The transverse vibration mode is excited and the resonant frequency is derived in the same way Referring to FIG. 7, the upper end of rock bolt 10 is threaded into an expansion nut 21 having circular sharp edges which dig into the rock lining predrilled hole 12 as bolt head 13 is turned to increase the tension in the bolt. A low tension is therefore indicative of a poorly anchored bolt. The bolt integrity testing device is the same as for resin grouted bolts with the exception that only accelerometer 18 is needed to sense transverse vibrations. The applicable frequency equation is:

$$f = f_i(1 + cT)^{1/2} \quad (3)$$

where
$f_i$ = the resonant frequency of the transverse vibration mode as given by equation (2),
$c$ = a constant, and
$T$ = the tension.

Figure 8:
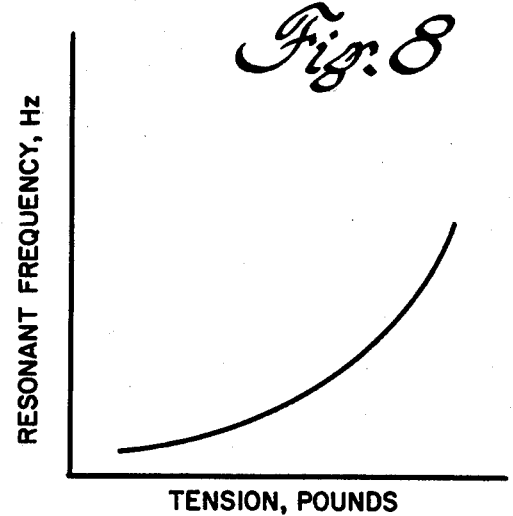
FIG. 8 is a curve of resonant frequency of the transverse mode versus tension in expansion nut bolts.

In practicing the method, bolt base 13 is tapped by hammer 16 in the transverse direction to induce broad band sound vibrations, and bolt vibrations in the transverse direction are sensed by accelerometer 18 and converted to a corresponding electrical signal. The signal amplitude is measured at a plurality of adjacent, narrow frequency bands, typically 10 Hz wide, and the resonant frequency of the transverse vibration mode is obtained. Conversion to tension in pounds is made by using the curve in FIG. 8 of resonant frequency in hertz versus tension.

While the invention has been particularly shown and described with reference to several preferred embodiments thereof, it will be understood by those skilled in the art that various changes in form and details may be made therein without departing from the spirit and scope of the invention.

What is claimed is:

1. A method of testing the integrity of the anchoring of a rock bolt anchored within an elongated hole in a rock-like substance and having an externally accessible base comprising the steps of
    striking the base of said rock bolt to induce acoustic vibrations therein and excite at least one selected vibration mode thereof,
    sensing the vibrations of said rock bolt and generating an electrical signal representative of said vibrations, and
    measuring the amplitude of said electrical signal at a plurality of discrete narrow frequency bands covering a predetermined frequency range and deriving the resonant frequency of said selected vibration mode as an indication of the integrity of the anchoring of said rock bolt.

2. The method according to claim 1 wherein said rock bolt is made of metal, and the step of striking the base of said rock bolt is performed by tapping the base with a metal object.

3. The method according to claim 2 wherein said rock bolt is anchored within the elongated hole by means of grout material, the step of striking the base of said rock bolt excites the axial and transverse vibration modes, and the step of measuring the amplitude of said electrical signal at a plurality of discrete narrow frequency bands and deriving the resonant frequency comprises deriving the resonant frequency of both the axial and transverse vibration modes as an indication of the effective bonded bolt length and axial length of voids in said grout material.

4. The method according to claim 2 wherein said rock bolt is anchored within the elongated hole by means of an expansion nut threaded onto one end thereof, the step of striking the base of said rock bolt excites the transverse vibration mode, and the step of measuring the amplitude of said electrical signal at a plurality of discrete narrow frequency bands and deriving the resonant frequency comprises deriving the resonant frequency of the transverse vibration mode as an indication of the tension in said rock bolt.

5. A method of testing the bond integrity of a rock bolt bonded by resin grout within an elongated hole in rock strata and having an externally accessible base comprising the steps of
    striking the base of said rock bolt to induce broadband acoustic vibrations therein and excite the axial and transverse vibration modes thereof,
    sensing the vibrations of said rock bolt and generating an electrical signal representative of said vibrations, and measuring the amplitude of said electrical signal at a plurality of discrete narrow frequency bands covering a predetermined frequency range and deriving the resonant frequency of each vibration mode as an indication of the effective bonded bolt length and axial length of voids in said resin grout.

6. The method according to claim 5 wherein said rock bolt is made of metal, and the step of striking the base of said rock bolt is performing by tapping the base with a metal object.

7. The method according to claim 6 wherein the steps of striking the base of said rock bolt, sensing the vibrations and generating an electrical signal, and measuring the amplitude of said electrical signal at a plurality of discrete narrow frequency bands and deriving the resonant frequency are performed separately and sequentially for the axial and transverse vibration modes.

8. A method of testing the tension of a rock bolt having one end anchored by means of an expansion nut within an elongated hole in rock strata and having an externally accessible base comprising the steps of
striking the base of said rock bolt to induce broad band acoustic vibrations therein and excite the transverse vibration mode thereof,
sensing the vibrations of said rock bolt and generating an electrical signal representative thereof, and
measuring the amplitude of said electrical signal at a plurality of discrete narrow frequency bands covering a predetermined frequency range and deriving the resonant frequency of said transverse vibration mode as an indication of the tension in said rock bolt.

* * * * *